(12) United States Patent
Unuma et al.

(10) Patent No.: US 12,729,128 B2
(45) Date of Patent: Sep. 8, 2026

(54) CALCIUM CARBONATE SINTERED BODY AND METHOD FOR PRODUCING SAME, AND BONE GRAFTING MATERIAL

(71) Applicant: SHIRAISHI CENTRAL LABORATORIES CO. LTD., Amagasaki-city (JP)

(72) Inventors: Hidero Unuma, Yonezawa-city (JP); Toshitake Furusawa, Yonezawa-city (JP); Shota Umemoto, Amagasaki-city (JP); Masahiko Tajika, Amagasaki-city (JP)

(73) Assignee: SHIRAISHI CENTRAL LABORATORIES CO. LTD., Amagasaki-city (JP)

( * ) Notice: Subject to any disclaimer, the term of this patent is extended or adjusted under 35 U.S.C. 154(b) by 984 days.

(21) Appl. No.: 17/439,670

(22) PCT Filed: Mar. 9, 2020

(86) PCT No.: PCT/JP2020/009950
§ 371 (c)(1),
(2) Date: Sep. 15, 2021

(87) PCT Pub. No.: WO2020/189366
PCT Pub. Date: Sep. 24, 2020

(65) Prior Publication Data

US 2022/0153604 A1 May 19, 2022

(30) Foreign Application Priority Data

Mar. 19, 2019 (JP) ................................ 2019-051208

(51) Int. Cl.
*C01F 11/18* (2006.01)
*A61L 27/10* (2006.01)
(Continued)

(52) U.S. Cl.
CPC ............ *C01F 11/185* (2013.01); *A61L 27/10* (2013.01); *A61L 27/306* (2013.01); *B01J 20/043* (2013.01);
(Continued)

(58) Field of Classification Search
CPC . C01F 11/185; C01P 2004/03; C01P 2004/61; C01P 2006/12; C01P 2006/80; C01P 2004/64
See application file for complete search history.

(56) References Cited

U.S. PATENT DOCUMENTS 3,394,021 A * 7/1968 Bush ...................... C04B 30/00 106/286.6
3,417,172 A * 12/1968 Rostoker ................ C04B 14/26 264/122
(Continued)

FOREIGN PATENT DOCUMENTS

JP 54-28397 B2 9/1979
JP H08-266183 A 10/1996
(Continued)

OTHER PUBLICATIONS

Machine translation of JP-2007254240-A (Year: 2007).*
(Continued)

*Primary Examiner* — Anthony J Zimmer
*Assistant Examiner* — Logan Laclair
(74) *Attorney, Agent, or Firm* — WHDA, LLP

(57) ABSTRACT

Provided is a method for producing a calcium carbonate sintered body whereby a good sintered body can be obtained without having to use any sintering aid. A method for producing a calcium carbonate sintered body includes the steps of: compacting calcium carbonate to make a green body; heating the green body under a condition of a temperature of 500° C. or lower to remove an organic compo-
(Continued)

nent contained in the green body; and sintering the green body under conditions of a carbon dioxide atmosphere and a temperature of 450° C. or higher to obtain a calcium carbonate sintered body.

2 Claims, 4 Drawing Sheets

(51) Int. Cl.
*A61L 27/30* (2006.01)
*B01J 20/04* (2006.01)
*B01J 20/28* (2006.01)
*B01J 20/30* (2006.01)

(52) U.S. Cl.
CPC ... *B01J 20/28004* (2013.01); *B01J 20/28011* (2013.01); *B01J 20/28059* (2013.01); *B01J 20/3064* (2013.01); *B01J 20/3078* (2013.01); *A61L 2430/02* (2013.01); *C01P 2004/03* (2013.01); *C01P 2004/61* (2013.01); *C01P 2004/62* (2013.01); *C01P 2004/64* (2013.01); *C01P 2006/10* (2013.01); *C01P 2006/12* (2013.01); *C01P 2006/60* (2013.01); *C01P 2006/80* (2013.01)

(56) References Cited

U.S. PATENT DOCUMENTS

| | | | | | |
|---|---|---|---|---|---|
| 4,124,688 | A | | 11/1978 | Shibazaki et al. | |
| 5,187,125 | A | * | 2/1993 | Someya | C04B 35/6455 423/430 |
| 5,897,765 | A | | 4/1999 | Mercier | |
| 2018/0237300 | A1 | | 8/2018 | Sakai et al. | |
| 2019/0375687 | A1 | | 12/2019 | Tajika et al. | |
| 2020/0055783 | A1 | | 2/2020 | Tjika et al. | |
| 2020/0331770 | A1 | | 10/2020 | Unuma et al. | |

FOREIGN PATENT DOCUMENTS

| | | | | | |
|---|---|---|---|---|---|
| JP | 9-124379 | A | | 5/1997 | |
| JP | H11-501568 | A | | 2/1999 | |
| JP | H11-75609 | A | | 3/1999 | |
| JP | 2003-327468 | A | | 11/2003 | |
| JP | 2006-26616 | A | | 2/2006 | |
| JP | 2007-63085 | A | | 3/2007 | |
| JP | 2007254240 | A | * | 10/2007 | |
| JP | 2011-251886 | A | | 12/2011 | |
| JP | 2012-240872 | A | | 12/2012 | |
| JP | 2015-166075 | A | | 9/2015 | |
| JP | 2017214238 | A | * | 12/2017 | C01F 11/18 |
| WO | 2017/038360 | A1 | | 3/2017 | |
| WO | WO-2017209096 | A1 | * | 12/2017 | A01K 61/57 |
| WO | 2018/155680 | A1 | | 8/2018 | |
| WO | 2018/155681 | A1 | | 8/2018 | |

OTHER PUBLICATIONS

Machine translation of WO-2017209096-A1 (Year: 2017).*

McGee (Colorado Yule Marble—Building Stone of the Lincoln Memorial, US Geographical Survey Bulletin 2162, 1999) (Year: 1999).*

Machine Translation of JP-2017214238-A (Year: 2017).*

Office Action dated Feb. 14, 2023, issued in counterpart CN application No. 202080021903.1. (12 pages).

"Study Guide for Fundamentals of Materials Science", Wuhan University of Technology Press, Jul. 2019, p. 99. (3 pages).

Office Action dated Feb. 14, 2023, issued in counterpart JP application No. 2019-051208, with English translation. (10 pages).

Notification of Transmittal of Translation of the International Preliminary Report on Patentability (Form PCTIB/338) issued in counterpart International Application No. PCT/JP2020/009950 mailed Sep. 30, 2021 with Forms PCT/IB/373 and PCT/ISA/237. (7 pages).

Kuiyi, Rong et al., "Nonmetallic Minerals and Rock Materials Technology", Wuhan University of Technology Press, Jun. 1996, p. 119, with English Translation. (6 pages).

Office Action dated Jul. 20, 2022, issued in counterpart CN Application No. 202080021903.1, with English Translation. (24 pages).

Office Action dated Sep. 6, 2022, issued in counterpart CN Application No. 2019-051208, with English Translation. (12 pages).

Extended (Supplementary) European Search Report dated Nov. 11, 2022, issued in counterpart EP application No. 20772848.6. (12 pages).

Honma et al., "Fabrication of calcite (CaCO3) ceramics with high density", Journal of Materials Science Letters, 1998, vol. 17, No. 9, pp. 745-746, cited in EP Extended European Search Report dated Nov. 11, 2022. (2 pages).

Maruta et al., "Fabrication of low-crystalline carbonate apatite foam bone replacement based on phase transformation of calcite foam", Dental Materials Journal, 2011, vol. 30, No. 1, pp. 14-20, cited in EP Extended European Search Report dated Nov. 11, 2022. (7 pages).

International Search Report dated May 19, 2020, issued in counterpart International Application No. PCT/JP2020/009950. (3 pages).

Tomatsuri et al., "Effect of Starting Materials on Liquid Phase Sintering of Calcium Carbonate", Proceedings for the Academic Conference of the Society of Inorganic Materials, Japan, Nov. 14, 2002, vol. 105, pp. 46-47, cited in Specification (2 pages).

Office Action dated Dec. 5, 2025, issued in counterpart EP Application No. 20772848.6 (5 pages).

* cited by examiner

[FIG. 1.]
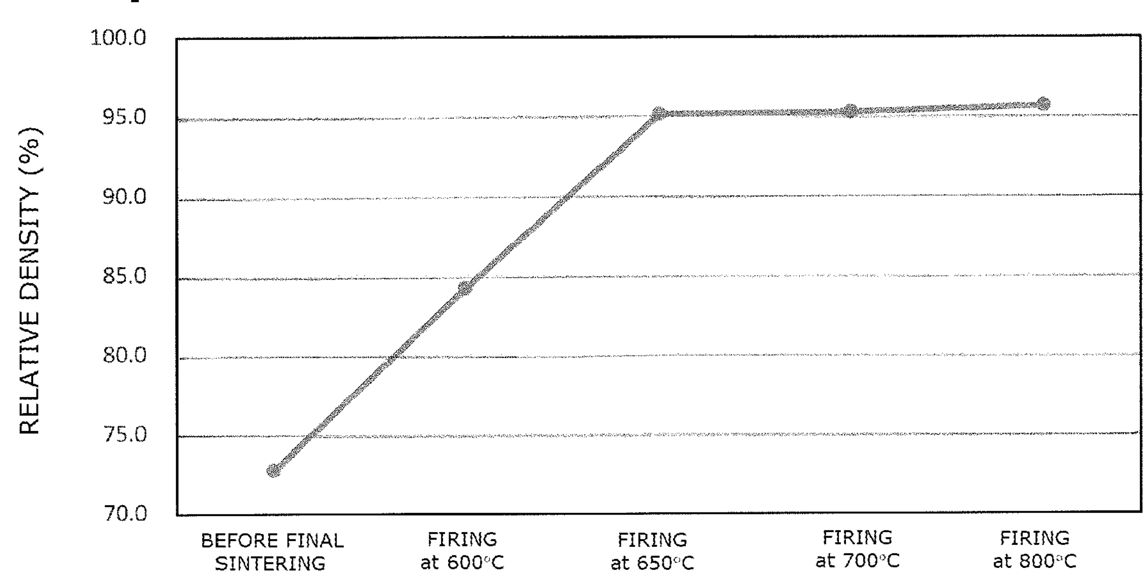
[FIG. 2.]
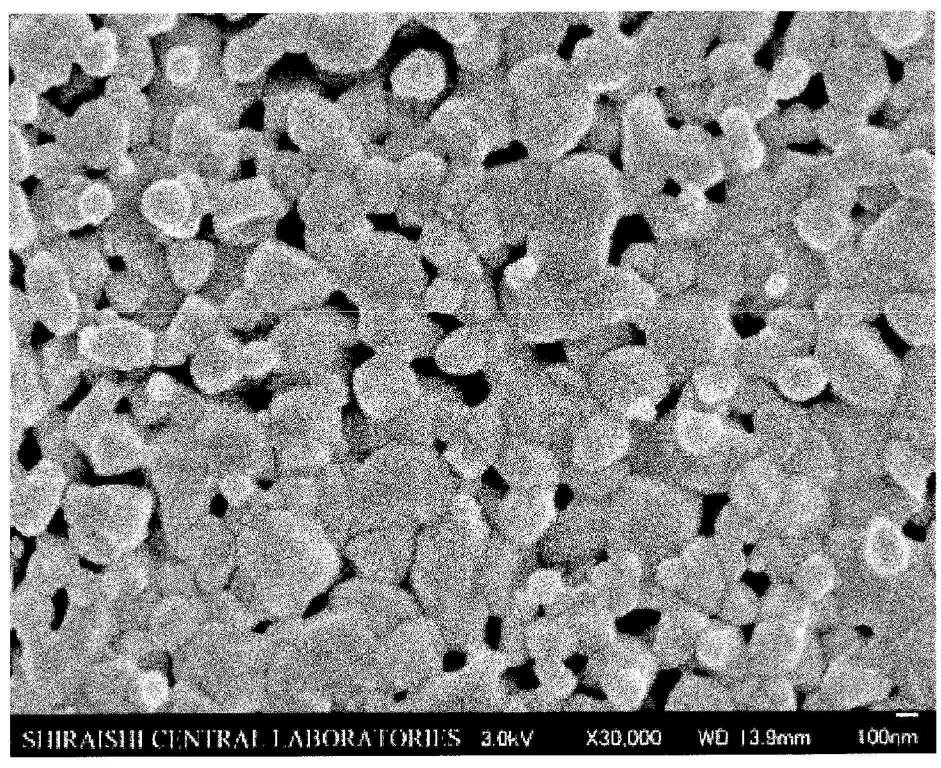

[FIG. 3.]
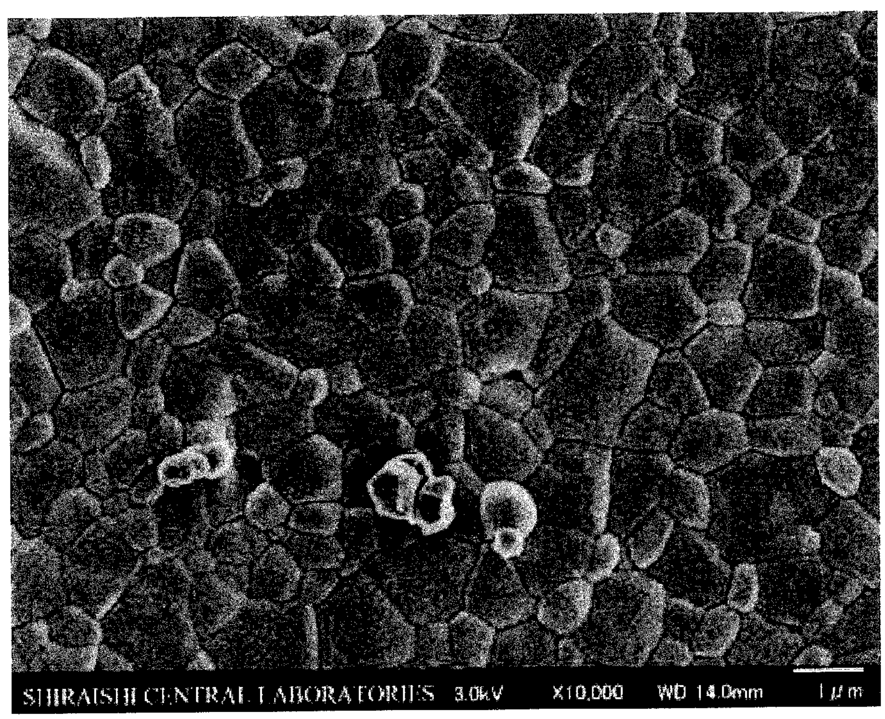
[FIG. 4.]
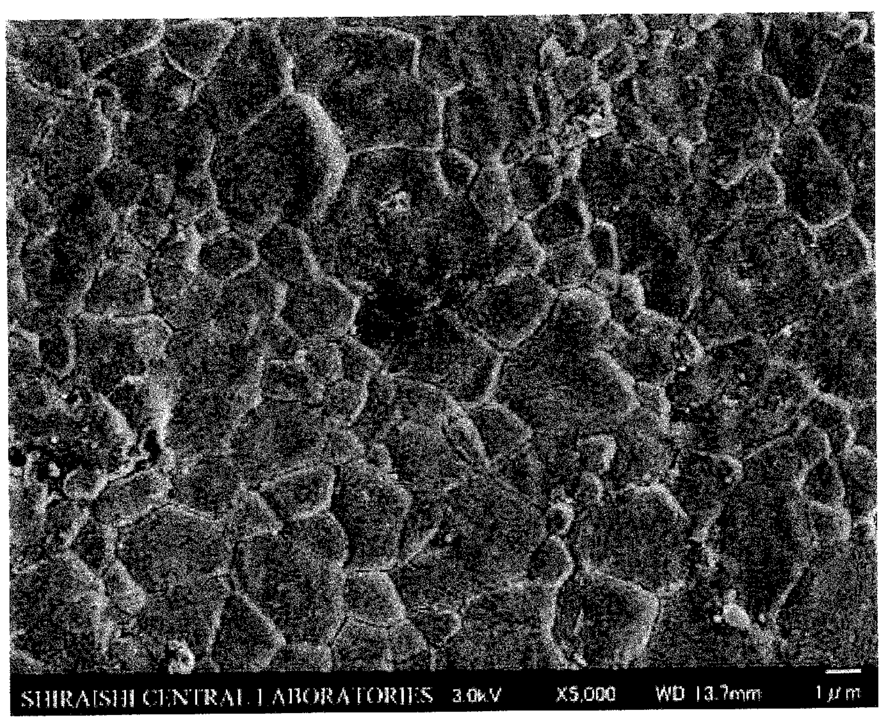

[FIG. 5.]
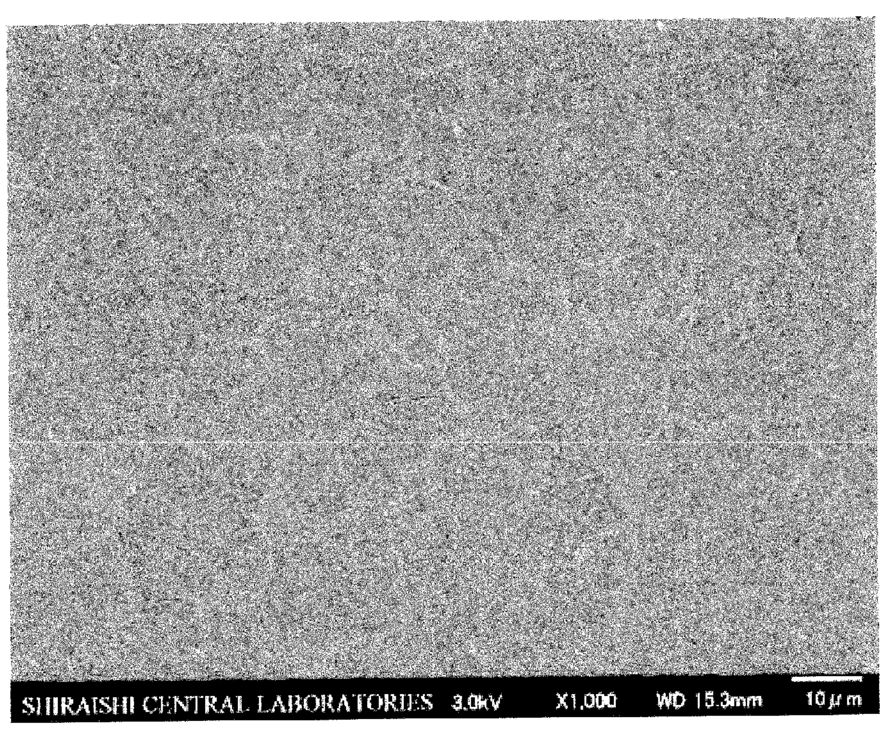
[FIG. 6.]
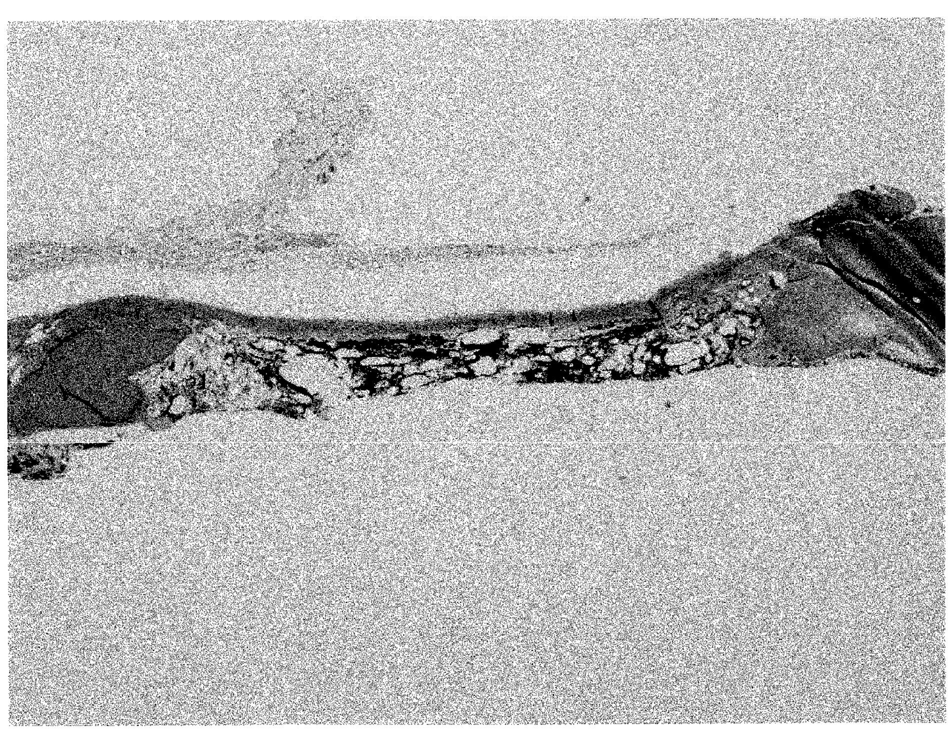

[FIG. 7.]
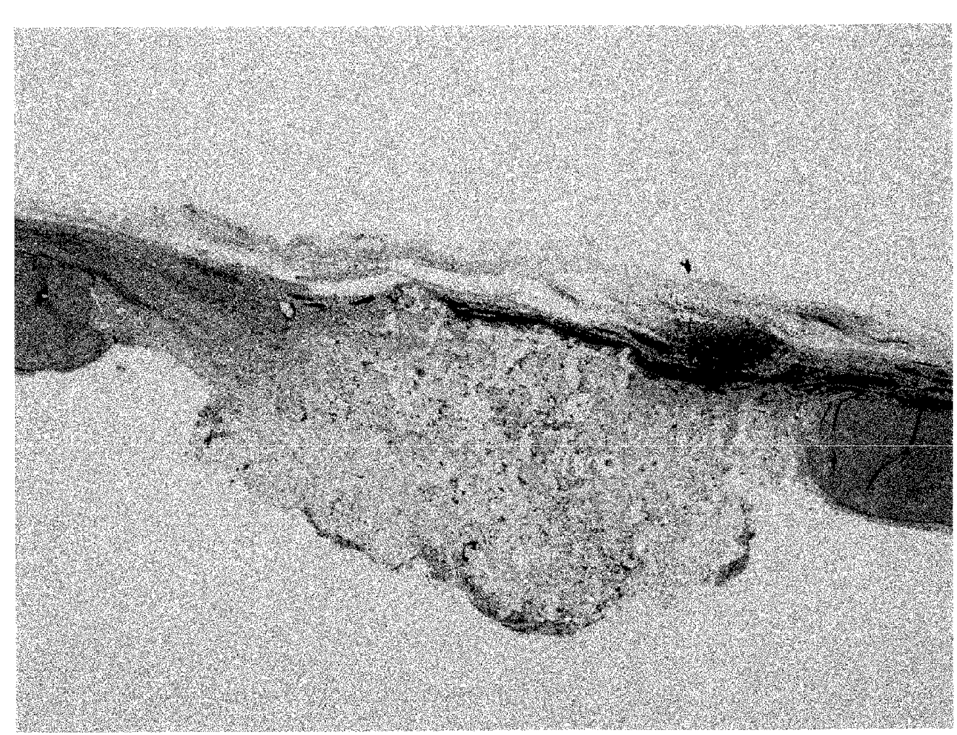
[FIG. 8.]
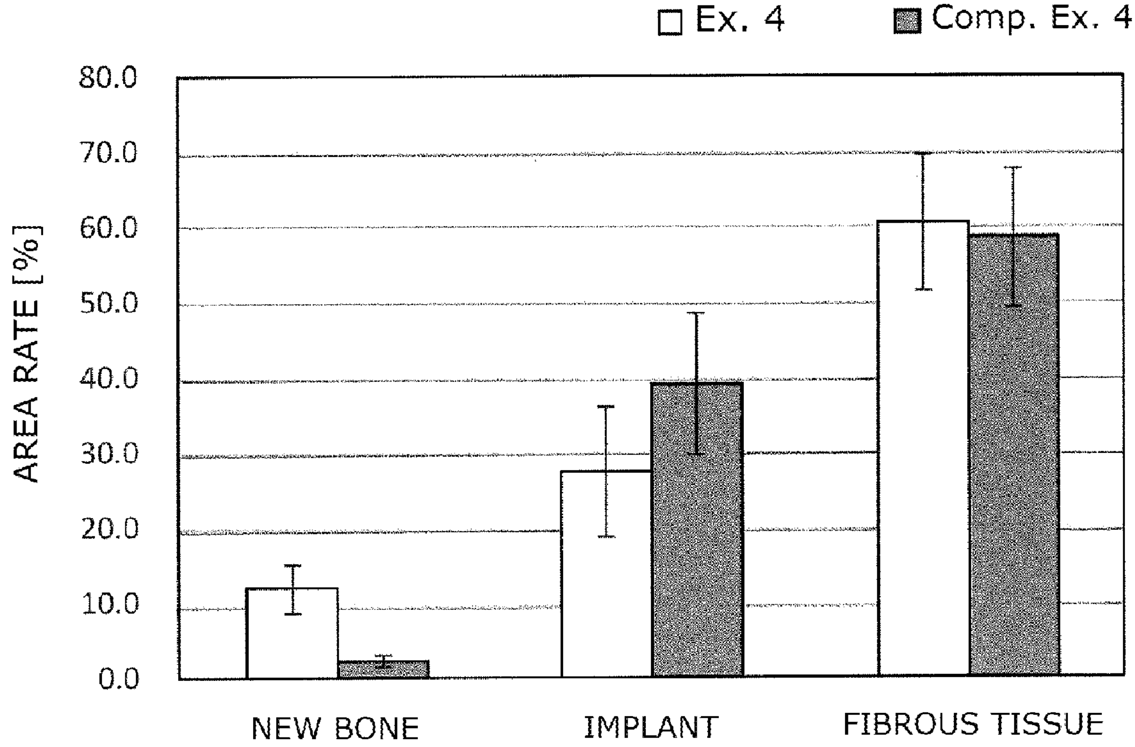

CALCIUM CARBONATE SINTERED BODY AND METHOD FOR PRODUCING SAME, AND BONE GRAFTING MATERIAL

TECHNICAL FIELD

The present invention relates to: calcium carbonate sintered bodies and methods for producing the same; porous calcium carbonate sintered bodies and methods for producing the same; and bone substitute materials, growing nuclei for cultured pearls, and water purifiers using calcium carbonate sintered bodies or porous calcium carbonate sintered bodies.

BACKGROUND ART

A calcium carbonate sintered body is expected to be applied to, for example, a material (artificial bones) for use to be substituted for bone defects to promote bone regeneration, a nucleus material for use to be implanted into mother shells as artificial nuclei for cultured pearls, or a water purifier for use to adsorb fluorine, phosphorus, and so on, and various studies have been done on its production method. In conventional methods for producing a calcium carbonate sintered body, generally, a calcium carbonate sintered body is produced by isostatically pressing a mixture of calcium carbonate and a sintering aid into a green body and sintering the green body in a carbon dioxide atmosphere (see Patent Literature 1 and Non-Patent Literature 1).

CITATION LIST

Patent Literature

Patent Literature 1: JP-A-2007-254240

Non-Patent Literature

Non-Patent Literature 1: Satoko Tomatsuri et al., "Effect of Starting Materials on Liquid Phase Sintering of Calcium Carbonate", Proceedings for the Academic Conference of the Society of Inorganic Materials, Japan, Vol. 105th, p. 46-47 (Nov. 14, 2002)

SUMMARY OF INVENTION

Technical Problem

In recent years, use of calcium carbonate for artificial bones as bone substitute materials and so on has been under consideration.

However, since the conventional methods for producing a calcium carbonate sintered body require a sintering aid as described above, they have difficulty in reducing the content of impurities. For this reason, the calcium carbonate sintered body may not be able to be used for biological applications, such as a bone substitute material.

Furthermore, in conventional methods for producing a porous calcium carbonate sintered body, obtained porous calcium carbonate sintered bodies may be colored.

Moreover, in a method for producing a high-purity calcium carbonate sintered body requiring no sintering aid, the density of the calcium carbonate sintered body may not be able to be sufficiently increased, in which case a good sintered body cannot be obtained.

An object of the present invention is to provide: a method for producing a calcium carbonate sintered body; a calcium carbonate sintered body; a method for producing a porous calcium carbonate sintered body; a porous calcium carbonate sintered body; and a bone substitute material, a growing nucleus for a cultured pearl, and a water purifier using a calcium carbonate sintered body or a porous calcium carbonate sintered body, which are capable of providing a good sintered body without having to use any sintering aid.

Solution to Problem

A calcium carbonate sintered body according to the present invention contains 99.5% by mass or more calcium carbonate and has an average particle diameter of 0.1 μm to 20 μm in a particle diameter distribution measured by scanning electron microscopy, a Vickers hardness of 50HV1.0 or more, and a relative density of 90% or more.

The calcium carbonate sintered body according to the present invention preferably contains 99.7% by mass or more calcium carbonate.

A method for producing a calcium carbonate sintered body according to the present invention preferably includes the steps of: compacting calcium carbonate to make a green body; heating the green body under a condition of a temperature of 500° C. or lower to remove an organic component contained in the green body; and sintering the green body under conditions of a carbon dioxide atmosphere and a temperature of 500° C. or higher to obtain a calcium carbonate sintered body.

In the method for producing a calcium carbonate sintered body according to the present invention, the heating of the green body under the condition of a temperature of 500° C. or lower is preferably performed in an oxygen gas atmosphere.

In the method for producing a calcium carbonate sintered body according to the present invention, the calcium carbonate preferably has an average particle diameter of 0.05 μm to 0.30 μm in a particle diameter distribution measured by transmission electron microscopy and a BET specific surface area of 5 $m^2/g$ to 25 $m^2/g$.

In the method for producing a calcium carbonate sintered body according to the present invention, the calcium carbonate preferably has a purity of 99.9% by mass or more.

A porous calcium carbonate sintered body according to the present invention contains 95% by mass or more calcium carbonate and has a porosity of 10% or more and a whiteness of 85 or more.

The porous calcium carbonate sintered body according to the present invention preferably contains 99% by mass or more calcium carbonate.

In the porous calcium carbonate sintered body according to the present invention, a connected pore leading to an exterior of the sintered body is preferably formed.

A method for producing a porous calcium carbonate sintered body according to the present invention includes the steps of: preparing a dispersion liquid containing calcium carbonate; adding a foaming agent to the dispersion liquid, followed by stirring until foamy to make a foam; heating the foam under a condition of a temperature of 500° C. or lower to remove an organic component contained in the foam; and sintering the foam under conditions of a carbon dioxide atmosphere and a temperature of 450° C. or higher to obtain a porous calcium carbonate sintered body.

In the method for producing a porous calcium carbonate sintered body according to the present invention, the heating of the foam under the condition of a temperature of 500° C. or lower is preferably performed in an oxygen gas atmosphere.

In the method for producing a porous calcium carbonate sintered body according to the present invention, the dispersion liquid preferably contains the calcium carbonate in an amount of 20% by volume or more.

A bone substitute material according to the present invention contains the calcium carbonate sintered body structured according to the present invention or the porous calcium carbonate sintered body structured according to the present invention in an amount of, in terms of calcium carbonate, 70% by weight or more of a total weight of the bone substitute material.

A bone substitute material according to the present invention having a surface partly or entirely coated with the calcium carbonate sintered body structured according to the present invention or the porous calcium carbonate sintered body structured according to the present invention.

A growing nucleus for a cultured pearl according to the present invention contains the calcium carbonate sintered body structured according to the present invention or the porous calcium carbonate sintered body structured according to the present invention in an amount of, in terms of calcium carbonate, 70% by weight or more of a total weight of the growing nucleus.

A water purifier according to the present invention contains the calcium carbonate sintered body structured according to the present invention or the porous calcium carbonate sintered body structured according to the present invention in an amount of, in terms of calcium carbonate, 70% by weight or more of a total weight of the water purifier.

Advantageous Effects of Invention

The method for producing a calcium carbonate sintered body and the method for producing a porous calcium carbonate sintered body according to the present invention enable provision of a good sintered body without having to use any sintering aid.

The calcium carbonate sintered body according to the present invention contains less impurities and, therefore, can be used for biological and like applications. In addition, the calcium carbonate sintered body according to the present invention is increased in density and is therefore increased in strength.

The porous calcium carbonate sintered body according to the present invention contains less impurities and, therefore, can be used for biological and like applications. In addition, the porous calcium carbonate sintered body according to the present invention is increased in whiteness.

The bone substitute material according to the present invention contains less impurities and is therefore increased in biological safety.

The growing nucleus for a cultured pearl according to the present invention can be easily controlled in size as compared to a natural shell which is currently mainly used and, therefore, can be produced in large numbers.

The water purifier according to the present invention is kept from becoming mushy in water with the aid of sintering and is therefore increased in usability and handleability.

BRIEF DESCRIPTION OF DRAWINGS

FIG. 1 is a graph showing relative density when only the sintering temperature is varied under conditions of Example 2.

FIG. 2 is a scanning electron micrograph at 30000-fold magnification showing a calcium carbonate sintered body obtained by final sintering at a sintering temperature of 600° C. for an hour.

FIG. 3 is a scanning electron micrograph at 10000-fold magnification showing a calcium carbonate sintered body obtained by final sintering at a sintering temperature of 650° C. for an hour.

FIG. 4 is a scanning electron micrograph at 5000-fold magnification showing a calcium carbonate sintered body obtained by final sintering at a sintering temperature of 700° C. for an hour.

FIG. 5 is a scanning electron micrograph at 1000-fold magnification showing a calcium carbonate sintered body obtained by final sintering at a sintering temperature of 800° C. for an hour.

FIG. 6 is a photograph showing a state of an observation sample made by implanting granules of a porous calcium carbonate sintered body of Example 4 into a skull of a male rat.

FIG. 7 is a photograph showing a state of an observation sample made by implanting granules of a β-TCP artificial bone of Comparative Example 4 into a skull of a male rat.

FIG. 8 is a graph showing calculation results of the area rates of new bones, implants, and fibrous tissues in the respective observation samples in Example 4 and Comparative Example 4.

DESCRIPTION OF EMBODIMENTS

Hereinafter, a description will be given of a preferred embodiment. However, the following embodiment is merely illustrative and the present invention is not limited to the following embodiment.

Method for Producing Calcium Carbonate Sintered Body

A method for producing a calcium carbonate sintered body according to the present invention includes the steps of: compacting calcium carbonate to make a green body; heating the green body under a condition of a temperature of 500° C. or lower to remove an organic component contained in the green body; and sintering the green body under conditions of a carbon dioxide atmosphere and a temperature of 450° C. or higher to obtain a calcium carbonate sintered body.

(Calcium Carbonate)

In calcium carbonate for use in the present invention, the average particle diameter ($D_{50}$) thereof in a particle diameter distribution measured by observation with a transmission electron microscope is preferably in a range of 0.05 μm to 0.50 μm, more preferably in a range of 0.05 μm to 0.30 μm, still more preferably in a range of 0.08 μm to 0.30 μm, and particularly preferably in a range of 0.10 μm to 0.25 μm. When the average particle diameter ($D_{50}$) is in the above range, a higher-density green body can be made and, therefore, a higher-density calcium carbonate sintered body can be produced. The particle diameter distribution through the observation with a transmission electron microscope can be determined by measuring 1000 or more calcium carbonate particles as a measurement target by observation with the transmission electron microscope.

Calcium carbonate for use in the present invention can be produced, for example, by a commonly well-known carbon dioxide synthesis method of blowing carbon dioxide into lime milk to react them with each other. In particular, particles having an average particle diameter ($D_{50}$) exceeding 0.1 μm can be produced according to the production method described in Japanese Patent No. 0995926.

The BET specific surface area of calcium carbonate for use in the present invention is preferably 5 $m^2/g$ to 25 $m^2/g$, more preferably 7 $m^2/g$ to 20 $m^2/g$, and still more preferably 8 $m^2/g$ to 15 $m^2/g$. When the BET specific surface area is in the above range, the sinterability of calcium carbonate can be further increased. Thus, a higher-density calcium carbonate sintered body can be produced.

The purity of calcium carbonate for use in the present invention is preferably 99.0% by mass or more, more preferably 99.5% by mass or more, and still more preferably 99.6% by mass or more.

In the present invention, high-purity calcium carbonate having a purity of 99.7% by mass or more may be used. With the use of such high-purity calcium carbonate, the sintered body can be more suitably used for biological applications requiring biological safety. In addition, the amount of sintering aid to be added in sintering can be made smaller. The purity of such calcium carbonate is preferably 99.8% by mass or more, more preferably 99.9% by mass or more, and still more preferably 99.95% by mass or more. Such high-purity calcium carbonate can be produced, for example, by the method disclosed in Japanese Patent Application Gazette No. 2012-240872.

Although no particular limitation is placed on the upper limit of the purity of calcium carbonate, it is generally 99.9999% by mass.

In addition, with the use of high-purity calcium carbonate, the sintering temperature can be lowered as compared to the use of less pure calcium carbonate.

(Green Body)

In the present invention, calcium carbonate powder is compacted to make a green body. The compaction is preferably uniaxial pressing. In the present invention, using a green body made by uniaxial pressing, a calcium carbonate sintered body having a high density can be produced. However, in the present invention, the making of a green body is not limited to uniaxial pressing and a green body may be made by any other known forming method, such as isostatic pressing, doctor blade technique or casting.

In the present invention, the relative density of the green body is preferably 50% or more, more preferably 55% or more, and still more preferably 58% or more. The relative density of the green body is a value obtained by dividing the bulk density of the green body by the theoretical density (2.711 $g/cm^3$) of calcium carbonate. The bulk density of the green body can be measured by the Archimedes' method to be described later. The relative density of the green body is preferably that obtained when the calcium carbonate powder is uniaxially pressed at a forming pressure of 196.1 Mpa (2000 $kgf/cm^2$). Within the above range of relative densities, a higher-density calcium carbonate sintered body can be obtained.

(Removal of Organic Component)

In the present invention, the above-described green body is heated under a condition of a temperature of 500° C. or lower. The above green body is preferably heated under a condition at 300° C. to 500° C. The heating may be performed in air, but is preferably performed in an oxygen gas atmosphere. The "oxygen gas atmosphere" above refers to an atmosphere having a higher oxygen concentration than the oxygen partial pressure concentration (approximately 20%) in the air. The concentration of oxygen gas (general gas) defined in the High-Pressure Gas Safety Act is 99.7%, and the method for distributing this type of oxygen gas into a furnace (irrespective of flow rate) is the simplest.

The heating time may be, for example, 2 hours to 24 hours.

The rate of temperature increase during the heating may be in a range of 2° C./min to 20° C./min. By the above heating, an organic component contained in the green body can be removed. An example of the organic component contained in the green body is a lubricant for use in forming. By removing thermally degraded organic component or carbonized organic component, the discoloration of an obtained calcium carbonate sintered body can be reduced. Thus, the whiteness of the obtained calcium carbonate sintered body can be increased.

(Production of Calcium Carbonate Sintered Body)

In the present invention, the above green body is sintered under conditions of a carbon dioxide atmosphere and a temperature of 500° C. or higher. Preferably, the above green body is sintered under the conditions at 500° C. to 950° C. The "carbon dioxide atmosphere" above refers to an atmosphere having a carbon dioxide partial pressure at which calcium carbonate is not decomposed into calcium oxide. Specifically, as an example, such a carbon dioxide partial pressure has been calculated with thermodynamic equilibrium calculation and phase diagram creation software "CaT-Calc" (developed by National Institute of Advanced Industrial Science and Technology) available from Materials Design Technology Co., Ltd. and shown in FIG. 3 in Patent Literature "Published Japanese Patent Application No. 2015-166075". According to this literature, assuming that the sintering temperature is 800° C., the carbon dioxide partial pressure is sufficient to be 0.3 atmospheres or more.

In using high-purity calcium carbonate having a purity of 99.7% by mass or more, the sintering temperature is preferably 500° C. to 800° C. and more preferably 650° C. to 800° C. If the sintering temperature is too low, sintering may not be able to sufficiently progress, so that the density cannot be increased. If the sintering temperature is too high, the obtained sintered body may cause cracks.

On the other hand, in using calcium carbonate having a purity of less than 99.7% by mass, the sintering temperature is preferably 800° C. to 900° C. If the sintering temperature is too low, sintering may not be able to sufficiently progress, so that the density cannot be increased. If the sintering temperature is too high, the obtained sintered body may swell.

No particular limitation is placed on the sintering time, but it is preferably an hour to ten hours and more preferably an hour to three hours. If the sintering time is too short, sintering may not be able to sufficiently progress, so that the density cannot be increased. If the sintering time is too long, the obtained sintered body may cause cracks or swell.

The rate of temperature increase during sintering is preferably in a range of 2° C./min to 20° C./min. Thus, it can be further reduced that the obtained sintered body causes cracks or swells.

In the present invention, by performing sintering under the above-described atmosphere, the amount of sintering aid necessary for sintering can be made small. Alternatively, without using any sintering aid, a good calcium carbonate sintered body can be obtained. Therefore, even with the use of calcium carbonate having a purity of less than 99.7% by mass, a higher-purity calcium carbonate sintered body can be obtained. In addition, by performing sintering under the above-described atmosphere, a good sintered body can be obtained and the obtained sintered body can be increased in density.

(Sintering Aid)

By performing sintering under the above-described atmosphere according to the present invention, the amount of sintering aid necessary for sintering can be made small.

Alternatively, without using any sintering aid, a calcium carbonate sintered body can be produced. Therefore, according to the present invention, the content of calcium carbonate in the sintered body can be increased, so that a higher-purity calcium carbonate sintered body can be produced.

However, a sintering aid may be used as necessary. Examples of the sintering aid include those containing carbonates of at least two of lithium, sodium, and potassium and having a melting point of 600° C. or lower. The melting point of the sintering aid is preferably 550° C. or lower, more preferably 530° C. or lower, and still more preferably in a range of 450° C. to 520° C. When the melting point of the sintering aid is in the above range, calcium carbonate can be fired at a lower temperature to produce a calcium carbonate sintered body. Because in the sintering the sintering aid is used by addition to calcium carbonate, the actual melting point becomes lower than the above temperature and, therefore, it sufficiently acts as a sintering aid. The sintering aid is preferably a mixture of potassium carbonate and lithium carbonate. For example, the melting point of the sintering aid can be determined from a phase diagram or can be measured by differential thermal analysis (DTA).

Alternatively, a mixture of potassium fluoride, lithium fluoride, and sodium fluoride may be used as a sintering aid. Such a mixture also preferably has the above range of melting points. Examples of such a sintering aid include mixtures having a composition range of 10% to 60% by mole potassium fluoride, 30% to 60% by mole lithium fluoride, and 0% to 30% by mole sodium fluoride. Within the above range, calcium carbonate can be fired at a lower temperature and a higher-density calcium carbonate sintered body can be produced.

In using a sintering aid, a mixture is preferably prepared by mixing calcium carbonate and the sintering aid so that the content of the sintering aid in the mixture of calcium carbonate and the sintering aid is 1.5% by mass or less, and the content of the sintering aid is more preferably 1.0% by mass or less, and still more preferably 0.7% by mass or less. If the content of the sintering aid is too large, the purity and density of the calcium carbonate sintered body may not be able to be increased.

Calcium Carbonate Sintered Body

In the present invention, the purity of the calcium carbonate sintered body is preferably 99.5% by mass or more, more preferably 99.7% by mass or more, still more preferably 99.8% by mass or more, yet still more preferably 99.9% by mass or more, even yet still more preferably 99.95% by mass or more, and particularly preferably 99.99% by mass or more. Thus, the calcium carbonate sintered body can also be used for biological and like applications. Although no particular limitation is placed on the upper limit of the purity of the calcium carbonate sintered body, it is generally 99.9999% by mass.

The relative density of the calcium carbonate sintered body is preferably 90% or more, more preferably 95% or more, still more preferably 97% or more, yet still more preferably 98% or more, and particularly preferably 99% or more. Although no particular limitation is placed on the upper limit of the relative density of the calcium carbonate sintered body, it is generally 99.9%.

In the calcium carbonate sintered body according to the present invention, the average particle diameter ($D_{50}$) in a particle diameter distribution measured by observation with a scanning electron microscope is in a range of 0.1 μm to 20 μm. The average particle diameter ($D_{50}$) in a particle diameter distribution measured by observation with a scanning electron microscope is preferably in a range of 0.2 μm to 15 μm, more preferably in a range of 0.3 μm to 10 μm, and still more preferably in a range of 0.5 μm to 5 μm. It is desirable that the particle diameter distribution through the observation with a scanning electron microscope is determined by measuring, from an image of the calcium carbonate sintered body observed as a measurement target with the scanning electron microscope, the sizes of 100 or more particles forming the sintered body. In doing so, it is desirable to measure particles in a cutaway section of the sintered body, but it is also possible to measure the sizes of particles on the surface of the sintered body and calculate 1.5 times the measured sizes as their particle diameters.

In the present invention, the Vickers hardness of the calcium carbonate sintered body is 50HV1.0 or more. The Vickers hardness of the calcium carbonate sintered body is preferably 90HV1.0 or more and more preferably 100HV1.0 or more.

The Vickers hardness can be measured according to the method described in JIS R 1610—Test methods for hardness of fine ceramics.

Since the calcium carbonate sintered body according to the present invention is increased in purity, it can be suitably used for biological applications, such as an artificial bone serving as a bone substitute material. In addition, the calcium carbonate sintered body can be suitably used for a growing nucleus for a cultured pearl or a water purifier.

Method for Producing Porous Calcium Carbonate Sintered Body

A method for producing a porous calcium carbonate sintered body according to the present invention includes the steps of: preparing a dispersion liquid containing calcium carbonate; adding a foaming agent to the dispersion liquid, followed by stirring until foamy to make a foam; heating the foam under a condition of a temperature of 500° C. or lower to remove an organic component contained in the foam; and sintering the foam under conditions of a carbon dioxide atmosphere and a temperature of 450° C. or higher to obtain a porous calcium carbonate sintered body.

(Calcium Carbonate)

Calcium carbonate described in relation to the above-described production of a calcium carbonate sintered body can be used as calcium carbonate here. Also in producing a porous calcium carbonate sintered body, with the use of high-purity calcium carbonate, the porous calcium carbonate sintered body can be more suitably used for biological applications requiring biological safety. In using a sintering aid, the same type and content of the sintering aid as those described above may be selected.

(Foaming Agent)

Examples of the foaming agent for use in the present invention include alkyl sulfate ester salts, such as triethanolamine lauryl sulfate, polyoxyethylene alkyl ether sulfate ester salts, polyoxyethylene alkyl ether acetates, and alkyl polyglucoside.

(Excipient)

In the present invention, an excipient may be added into the dispersion liquid. The addition of an excipient can increase the strength of bubbles in a dispersion foam obtained after foaming to stabilize the shape of the foam. Examples of the excipient include starch, dextrin, polyvinyl alcohol, polypropylene glycol, pectin, alginic acids, and sodium salts of carboxycellulose.

(Gelling Agent)

In the present invention, a gelling agent may be added into the dispersion liquid. When the dispersion liquid contains a gelling agent, the strength of bubbles in a dispersion foam obtained after foaming can be further increased to stabilize the shape of the foam. Examples of the gelling agent include polysaccharides, such as methylcellulose, and alkaline hydrosoluble polymers, such as isobutylene/maleic anhydride copolymer.

The content of gelling agent in the dispersion liquid is, relative to 100 parts by mass of calcium carbonate, preferably in a range of 0.1 to 5 parts by mass and more preferably in a range of 0.5 parts to 3 parts by mass. If the content of gelling agent is too small, the strength of bubbles in the foam does not increase, so that the shape of the foam may not be able to be stabilized. If the content of gelling agent is too large, the above effect proportional to the content thereof may not be able to be achieved.

(Dispersion Liquid)

In the present invention, calcium carbonate is preferably dispersed into a dispersion medium, such as water, using a device having a high stirring force, such as a disperser, a mixer or a ball mill, with gradual addition of calcium carbonate into the dispersion medium. The content of calcium carbonate is generally preferably 30% to 70% by mass in the dispersion liquid. In doing so, if necessary, about 0 parts to about 3 parts by mass of polymeric surfactant, such as a polyacrylate, relative to 100 parts by mass of calcium carbonate may be added as a dispersant into the dispersion liquid.

(Making of Foam)

In the present invention, the foaming agent is added to the above dispersion liquid and the mixture is then stirred until foamy, thus making a foam. The addition of the foaming agent is preferably performed so that the concentration of the foaming agent in the dispersion liquid reaches about 0.01% to about 5% by mass. The stirring is preferably performed with a handheld mixer, a disperser or the like. When the stirring is performed, the temperature of the dispersion liquid may increase. If necessary, the stirring may be performed with cooling of the dispersion liquid.

(Removal of Organic Component in Foam)

In the present invention, the above foam is heated under a condition of a temperature of 500° C. or lower. Preferably, the above foam is heated under a condition of a temperature of 300° C. to 500° C. The heating may be performed in air, but is preferably performed in an oxygen gas atmosphere. The "oxygen gas atmosphere" above refers to an atmosphere having a higher oxygen concentration than the oxygen partial pressure concentration (approximately 20%) in the air. The concentration of oxygen gas (general gas) defined in the High-Pressure Gas Safety Act is 99.7%, and the method for distributing this type of oxygen gas into a furnace (irrespective of flow rate) is the simplest.

The heating time may be, for example, 2 hours to 24 hours.

The rate of temperature increase during the heating may be in a range of 2° C./min to 20° C./min. By the above heating, an organic component contained in the foam can be removed. Examples of the organic component contained in the foam include a foaming agent, an excipient, a gelling agent, and a dispersant. By removing thermally degraded organic component or carbonized organic component, the discoloration of an obtained porous calcium carbonate sintered body can be reduced. Thus, the whiteness of the obtained porous calcium carbonate sintered body can be increased. In addition, the mechanical strength of the obtained porous calcium carbonate sintered body can be increased.

(Sintering of Foam)

In the present invention, the above foam is sintered under conditions of a carbon dioxide atmosphere and a temperature of 450° C. or higher. Preferably, the above foam is sintered under conditions of a carbon dioxide atmosphere and a temperature of 450° C. to 950° C. The "carbon dioxide atmosphere" above refers to an atmosphere having a carbon dioxide partial pressure at which calcium carbonate is not decomposed into calcium oxide. Specifically, as an example, such a carbon dioxide partial pressure has been calculated with thermodynamic equilibrium calculation and phase diagram creation software "CaTCalc" (developed by National Institute of Advanced Industrial Science and Technology) available from Materials Design Technology Co., Ltd. and shown in FIG. 3 in Patent Literature "Published Japanese Patent Application No. 2015-166075". According to this literature, assuming that the sintering temperature is 800° C., the carbon dioxide partial pressure is sufficient to be 0.3 atmospheres or more.

In using high-purity calcium carbonate having a purity of 99.7% by mass or more, the sintering temperature is preferably 500° C. to 800° C. and more preferably 650° C. to 800° C. If the sintering temperature is too low, sintering may not be able to sufficiently progress, so that the density cannot be increased. If the sintering temperature is too high, the obtained porous sintered body may cause cracks.

On the other hand, in using calcium carbonate having a purity of less than 99.7% by mass, the sintering temperature is preferably 800° C. to 900° C. If the sintering temperature is too low, sintering may not be able to sufficiently progress. If the sintering temperature is too high, the obtained porous sintered body may swell.

No particular limitation is placed on the sintering time, but it is preferably an hour to twelve hours and more preferably an hour to three hours. If the sintering time is too short, sintering may not be able to sufficiently progress. If the sintering time is too long, the obtained porous sintered body may cause cracks or swell.

The rate of temperature increase during sintering is preferably in a range of 2° C./min to 20° C./min. Thus, it can be further reduced that the obtained porous sintered body causes cracks or swells.

In the present invention, by performing sintering under the above-described atmosphere, the amount of sintering aid necessary for sintering can be made small. Alternatively, without using any sintering aid, a good porous calcium carbonate sintered body can be obtained. Therefore, even with the use of calcium carbonate having a purity of less than 99.7% by mass, a higher-purity porous calcium carbonate sintered body can be obtained. In addition, by performing sintering under the above-described atmosphere, a good porous sintered body can be obtained.

Porous Calcium Carbonate Sintered Body

The purity of the porous calcium carbonate sintered body according to the present invention is 95% by mass or more. The purity of the porous calcium carbonate sintered body is preferably 99% by mass or more, more preferably 99.5% by mass or more, still more preferably 99.7% by mass or more, yet still more preferably 99.8% by mass or more, even still more preferably 99.9% by mass or more, even yet still more preferably 99.95% by mass or more, and particularly preferably 99.99% by mass or more. Thus, the porous calcium carbonate sintered body can also be used for biological and like applications. Although no particular limitation is placed on the upper limit of the purity of the porous calcium carbonate sintered body, it is generally 99.9999% by mass.

The porosity of the porous calcium carbonate sintered body is 10% by volume or more. Although no particular limitation is placed on the upper limit of the porosity of the porous calcium carbonate sintered body, it is generally 95% by volume. By increasing the porosity, the porous calcium carbonate sintered body can be increased in bioabsorbability when used for an artificial bone as a bone substitute material, but, on the other hand, decreases its strength. Therefore, it is desirable to use the porous calcium carbonate sintered body by adjusting its porosity appropriately according to the application or case.

In the present invention, the whiteness of the porous calcium carbonate sintered body is 85 or more. The whiteness of the porous calcium carbonate sintered body is preferably 90 or more. Although no particular limitation is placed on the upper limit of the whiteness of the porous calcium carbonate sintered body, it may be, for example, 100.

The whiteness can be measured with a whiteness meter, a spectro-photometer or the like. The basic principle of the measurement is to irradiate the surface of a sample uniformly filled in a cell with light limited to a certain wavelength range through a specific filter and measure the whiteness by comparison of the amount of light reflected in a direction of 45 degrees from the sample surface with the amount of light reflected from a standard white plate.

In the porous calcium carbonate sintered body according to the present invention, a connected pore leading to the exterior of the sintered body is preferably formed. Thus, calcium carbonate inside of the porous sintered body can be easily brought into contact with the outside atmosphere. Therefore, the porous calcium carbonate sintered body can be more suitably used, for example, for biological or like applications.

Since the porous calcium carbonate sintered body according to the present invention is increased in purity, it can be suitably used for biological applications, such as an artificial bone serving as a bone substitute material. In addition, the porous calcium carbonate sintered body can be suitably used for a growing nucleus for a cultured pearl or a water purifier.

Bone Substitute Material and Others

A bone substitute material according to the present invention contains the calcium carbonate sintered body according to the present invention or the porous calcium carbonate sintered body according to the present invention in an amount of 70% by weight or more, in terms of calcium carbonate, of the total weight of the bone substitute material. Furthermore, the surface of the bone substitute material according to the present invention is partly or entirely coated with the calcium carbonate sintered body according to the present invention or the porous calcium carbonate sintered body according to the present invention. Therefore, the bone substitute material contains less impurities and is therefore increased in biological safety. In addition, the bone substitute material is excellent in mechanical strength and osteogenic ability.

A growing nucleus for a cultured pearl according to the present invention contains the calcium carbonate sintered body according to the present invention or the porous calcium carbonate sintered body according to the present invention in an amount of 70% by weight or more, in terms of calcium carbonate, of the total weight of the growing nucleus.

A water purifier according to the present invention contains the calcium carbonate sintered body according to the present invention or the porous calcium carbonate sintered body according to the present invention in an amount of 70% by weight or more, in terms of calcium carbonate, of the total weight of the water purifier.

EXAMPLES

Hereinafter, a description will be given of specific examples according to the present invention, but the present invention is not limited to these examples.

Production of Calcium Carbonate Sintered Body

Example 1

(Calcium Carbonate)

Calcium carbonate having a purity of 99% by mass, an average particle diameter ($D_{50}$) of 0.15 μm, and a BET specific surface area of 15 $m^2/g$ was used. The purity was derived by the difference method. Specifically, the respective amounts of impurities in a sample liquid for measurement in which a sample of known mass was dissolved were measured with an inductively coupled plasma emission spectrometer, the sum of the measurement results was considered as the content of impurities, and a value obtained by subtracting the content of impurities from the total mass was defined as the purity.

The average particle diameter ($D_{50}$) was determined by measuring the particle diameters of 1500 particles of calcium carbonate, which is a measurement target, by transmission electron microscope observation and using the obtained particle diameter distribution.

The BET specific surface area was measured by the single point method using FlowSorb 2200 manufactured by Shimadzu Corporation.

Using the above calcium carbonate, a calcium carbonate sintered body was produced in the following manner.

(Making of Green Body)

Calcium carbonate was wet mixed with a small amount of ethanol added thereto, thus making a raw material powder. The raw material powder was put into a cylindrical die and uniaxially pressed into shape using a press. The raw material powder was preliminarily pressed at a forming pressure of 98 Mpa (1000 $kgf/cm^2$) for one minute and then pressed at a forming pressure of 196.1 Mpa (2000 $kgf/cm^2$) for one minute.

(Heating and Firing of Green Body)

The obtained green body was increased in temperature to 500° C. at a rate of 5° C. per minute in an air atmosphere (21% oxygen concentration) and held for 12 hours after the temperature increase to remove an organic component. The green body was thereafter cooled, then increased in temperature to a sintering temperature (800° C.) at the same rate of temperature increase in a carbon dioxide atmosphere (100% carbon dioxide concentration), and finally sintered for an hour after the temperature increase, thus obtaining a calcium carbonate sintered body.

(Measurement of Relative Density of Calcium Carbonate Sintered Body)

The bulk density $\rho_b$ [$g/cm^3$] of the calcium carbonate sintered body was obtained by the Archimedes' method and the obtained bulk density was divided by the theoretical density (2.711 $g/cm^3$) of calcium carbonate to obtain its relative density. The bulk density of the calcium carbonate sintered body was obtained as follows. First, the dry weight $W_1$ of a sample of the calcium carbonate sintered body was measured, the sample was allowed to stand for about 10 minutes in paraffin warmed in a vessel put in hot water, then picked up from the vessel, and cooled to ordinary temperature. After getting cool, the weight $W_2$ of the sample containing paraffin was measured. Thereafter, the weight $W_3$ of the sample in water was measured and the bulk density $\rho_b$ of the sample was then determined from the following equation. The relative density of the calcium carbonate sintered body is shown in Table 1.

$$\text{Bulk Density } \rho_b\ [g/cm^3]=W_1\rho_w/(W_2-W_3)$$

$\rho_w$: water density [$g/cm^3$]

$W_1$: dry weight [g] of sample $W_2$: weight [g] of sample containing paraffin $W_3$: weight [g] of sample in water (Measurement of Average Particle Diameter of Calcium Carbonate Sintered Body)

The average particle diameter of the calcium carbonate sintered body was determined by measuring the particle diameters of 150 particles of calcium carbonate, which is a measurement target, by scanning electron microscope observation and using the obtained particle diameter distribution.

(Measurement of Purity of Calcium Carbonate Sintered Body)

The purity of the calcium carbonate sintered body was derived by the above-described difference method.

The purity of the calcium carbonate sintered body is shown in Table 1.

Example 2

Calcium carbonate having a purity of 99.9% by mass, an average particle diameter ($D_{50}$) of 0.1 μm, and a BET specific surface area of 18 $m^2/g$ was used. Furthermore, a green body obtained in the same manner as in Example 1 was increased in temperature to 500° C. at a rate of 5° C. per minute in an air atmosphere (21% oxygen concentration) and held for 12 hours after the temperature increase to remove an organic component. The green body was thereafter cooled, then increased in temperature to a sintering temperature (700° C.) at the same rate of temperature increase in a carbon dioxide atmosphere (100% carbon dioxide concentration), and finally sintered for an hour after the temperature increase, thus obtaining a calcium carbonate sintered body. The relative density, average particle diameter, and purity of the calcium carbonate sintered body are shown in Table 1.

FIG. 1 is a graph showing relative density when only the sintering temperature is varied under conditions of Example 2. In addition, for comparison, FIG. 1 also shows the relative density before sintering. It is seen from FIG. 1 that the relative density is approximately 95% or more when the sintering temperature is 650° C. to 800° C.

FIG. 2 is a scanning electron micrograph at 30000-fold magnification showing a calcium carbonate sintered body obtained by final sintering at a sintering temperature of 600° C. for an hour. FIG. 3 is a scanning electron micrograph at 10000-fold magnification showing a calcium carbonate sintered body obtained by final sintering at a sintering temperature of 650° C. for an hour. FIG. 4 is a scanning electron micrograph at 5000-fold magnification showing a calcium carbonate sintered body obtained by final sintering at a sintering temperature of 700° C. for an hour. FIG. 5 is a scanning electron micrograph at 1000-fold magnification showing a calcium carbonate sintered body obtained by final sintering at a sintering temperature of 800° C. for an hour.

FIGS. 2 to 4 show that good calcium carbonate sintered bodies were obtained, but FIG. 5 shows that particles excessively grew and the calcium carbonate sintered body thus slightly caused cracks.

Comparative Example 1

Calcium carbonate of Example 1 and a sintering aid were mixed to give a content of sintering aid of 0.6% by mass and the mixed powder was put together with a suitable amount of zirconia beads into a polyethylene bottle and dry mixed overnight to obtain a raw material powder. As the sintering aid, a mixture of potassium fluoride, lithium fluoride, and sodium fluoride was used. The mixing ratio of components of the mixture was, in terms of molar ratio, (potassium fluoride):(lithium fluoride):(sodium fluoride)=40:49:11. The melting point (eutectic temperature) of the mixture was 463° C. A green body obtained in the same manner as in Example 1 except for the use of the above raw material powder was increased in temperature to 400° C. at a rate of 5° C. per minute in an air atmosphere (21% oxygen concentration) and held for 12 hours after the temperature increase. The green body was thereafter cooled, then increased in temperature to a sintering temperature (480° C.) at the same rate of temperature increase in an air atmosphere (0.03% carbon dioxide concentration), and finally sintered for three hours after the temperature increase, thus obtaining a calcium carbonate sintered body. The relative density and purity of the calcium carbonate sintered body are shown in Table 1.

Comparative Example 2

A green body obtained in the same manner as in Example 2 was increased in temperature to 500° C. at a rate of 10° C. per minute in an air atmosphere (21% oxygen concentration) and finally sintered by holding it for 12 hours after the temperature increase, thus obtaining a calcium carbonate sintered body. The relative density, average particle diameter, and purity of the calcium carbonate sintered body are shown in Table 1.

Example 3

An amount of 434 parts by mass of calcium carbonate of Example 1 was dispersed into a dispersion medium obtained by previously mixing 2.4 parts by mass of methylcellulose and 11.0 parts by mass of special polycarboxylate polymer type surfactant (solid content: 4.4 parts by mass) into 238 parts by mass of ion-exchange water with a homogenizer-disperser, thus obtaining a dispersion liquid. Methylcellulose is a gelling agent and the special carboxylate polymer type surfactant is a dispersant. The obtained dispersion liquid was stirred until foamy at 1000 rpm for 10 minutes with a handheld mixer, thus making a foam. The foam was put into a forming mold made from paper, the forming mold was moved into a hot-air dryer, and the foam was heated at 80° C. for 0.5 hours in the hot-air dryer to turn the foam into a gel. The gelled foam was heated at 80° C. for 12 hours, thus obtaining a dried foam. The obtained dried foam was increased in temperature to 500° C. at a rate of temperature increase of 5° C./min in an oxygen atmosphere (100% oxygen concentration) and subjected to degreasing and sintering for 12 hours after the temperature increase. The whiteness of the obtained porous calcium carbonate sintered body is shown in Table 1. The whiteness was evaluated with a spectro-photometer.

Comparative Example 3

A dried foam made in the manner described in Example 3 was increased in temperature to a temperature (400° C.) at a rate of temperature increase of 5° C./min in an air atmosphere (21% oxygen concentration) and degreased for 10 hours after the temperature increase. Next, the foam was increased in temperature from 400° C. to a firing temperature (510° C.) at the same rate of temperature increase, finally fired for three hours after the temperature increase, and then cooled to room temperature at a rate of 10° C./min, thus obtaining a porous calcium carbonate sintered body. The whiteness of the obtained porous calcium carbonate sintered body is shown in Table 1.

Example 4

A dried foam made in the manner described in Example 3 was grounded into granules of about 1 mm to 2 mm diameter, increased in temperature to 500° C. at a rate of temperature increase of 5° C./min in an oxygen atmosphere (100% oxygen concentration), and degreased for 12 hours after the temperature increase to obtain a degreased product, and the obtained degreased product was cooled, then increased in temperature to a sintering temperature (800° C.) at the same rate of temperature increase in a carbon dioxide atmosphere (100% carbon dioxide concentration), and finally sintered for an hour after the temperature increase, thus obtaining granules of a porous calcium carbonate sintered body. A hole was drilled substantially in the center of the frontal bone of the skull of an 11-week-old male rat with a 5 mm diameter trepan and the obtained granules of the porous calcium carbonate sintered body were implanted into the hole. The day after the implantation was set at the first day and the skull was picked up three weeks (21 days) after. After extra soft tissues located around the implant were removed, the remaining portion was fixed and preserved in 10% neutral buffered formalin, then subjected to formic acid decalcification, embedded in paraffin, and sliced into flakes, and the flakes were stained with hematoxylin-eosin, thus obtaining an observation sample. The condition of the observation sample is shown in FIG. 6. The implant, a fibrous tissue, and a new bone were identified in the observation sample. In the staining with hematoxylin-eosin, the fibrous tissue, the implant, and the new bone were indicated by pink, white, and blood-red, respectively, and, thus, these portions of the observation sample were able to be distinguished from each other.

Furthermore, six specimens implanted under the same conditions in the above case were each calculated in terms of area rates of a new bone, an implant, and a fibrous tissue in the observation sample. The calculation results are shown in FIG. 8. The area rates (%) were calculated by enlarging the photograph shown in FIG. 6, determining the respective areas of the new bone, the implant, and the fibrous tissue from the enlarged photograph, and calculating the rates of the respective areas of the new bone, the implant, and the fibrous tissue to the total sum of the areas of the new bone, the implant, and the fibrous tissue. The area of each of the above portions was determined by marking the portion with a paint tool and binarizing it with ImageJ.

Comparative Example 4

Commercially available β-TCP artificial bone granules were implanted into the skull of a male rat in the same manner as in Example 4, thus making an observation sample. The condition of the observation sample is shown in FIG. 7. The calculation results of the area rates of a new bone, an implant, and a fibrous tissue in the observation sample are shown in FIG. 8. A comparison of the above results with the results of Example 4 using the Wilcoxon rank-sum test showed that the area rate of the new bone in Example 4 was higher at a significance level of 0.01, the area rate of the implant in Comparative Example 4 was higher at a significance level of 0.05, and there was no significant difference in the area rate of fibrous tissue between Example 4 and Comparative Example 4. It can be considered from the above comparison that the granules implanted in Example 4 are a material which has a higher ability for bone regeneration in a living organism and is more rapidly absorbable into the living organism than existing artificial bone products.

TABLE 1

| | Conditions | | | | | | Physical Properties |
|---|---|---|---|---|---|---|---|
| | Addition of Sintering Aid | Degreasing Atmosphere | Degreasing Temperature | Firing Atmosphere | Firing Temperature | Firing Time | Relative Density |
| Example 1 | not added | Air | 500° C. | $CO_2$ | 800° C. | 1 h | 95% |
| Example 2 | not added | Air | 500° C. | $CO_2$ | 700° C. | 1 h | 95% |
| Example 3 (Porous body) | not added | $O_2$ | 500° C. | — | — | — | — |
| Comparative Example 1 | added | Air | 400° C. | Air | 480° C. | 3 h | 95% |
| Comparative Example 2 | not added | undegreased | undegreased | Air | 500° C. | 12 h | 73% |
| Comparative Example 3 (Porous body) | not added | Air | 400° C. | Air | 510° C. | 3 h | — |

| | Physical Properties | | | | |
|---|---|---|---|---|---|
| | Average Particle Diameter After Firing | Calcium Carbonate Content in Sintered Body | Vickers Hardness | Porosity (%) | Whiteness (Porous body) |
| Example 1 | 1.7 μm | 99.5% | 130HV1.0 | — | — |
| Example 2 | 2.4 μm | 99.9% | 140HV1.0 | — | — |
| Example 3 (Porous body) | — | 98.0% | — | 65.0% | 89.5 |

TABLE 1-continued

| | | | | | |
|---|---|---|---|---|---|
| Comparative Example 1 | 1.2 μm | 99% | 90HV1.0 | — | — |
| Comparative Example 2 | 0.27 μm | 99.9% | 94HV1.0 | — | — |
| Comparative Example 3 (Porous body) | — | 98.0% | — | 65.0% | 74.8 |

The invention claimed is:

1. A method for producing a calcium carbonate sintered body, the method comprising the steps of: compacting calcium carbonate to make a green body; heating the green body under a condition of a temperature of 500° C. or lower in an oxygen gas atmosphere to remove an organic component contained in the green body; and sintering the green body under conditions of a carbon dioxide atmosphere and a temperature of 500° C. or higher without adding a sintering aid, or adding a sintering aid so that the content of the sintering aid is 1.5% by mass or less in the mixture of the calcium carbonate and the sintering aid to obtain a calcium carbonate sintered body, wherein in using high-purity calcium carbonate having a purity of 99.7% by mass or more, the sintering temperature of the green body is 650° C. to 800° C., and in using calcium carbonate having a purity of less than 99.7% by mass, the sintering temperature of the green body is 800° C. to 900° C., and wherein the calcium carbonate has an average particle diameter of 0.05 μm to 0.30 μm in a particle diameter distribution measured by transmission electron microscopy and a BET specific surface area of 5 $m^2/g$ to 25 $m^2/g$.

2. The method for producing a calcium carbonate sintered body according to claim 1, wherein the calcium carbonate has a purity of 99.9% by mass or more.

* * * * *